United States Patent [19]

Kuhn et al.

[11] Patent Number: 5,286,743

[45] Date of Patent: Feb. 15, 1994

[54] N-AMINOALKYLCARBONYLOXYALKYL-PYRROLE INSECTICIDAL ACARICIDAL AND MOLLUSCICIDAL AGENTS

[75] Inventors: David G. Kuhn, Newtown; Stephen F. Donovan, Yardley, both of Pa.; Joseph A. Furch, Lawrenceville, N.J.

[73] Assignee: American Cyanamid Company, Wayne, N.J.

[21] Appl. No.: 966,992

[22] Filed: Oct. 27, 1992

[51] Int. Cl.$^5$ ................ C07D 207/34; C07D 207/36; A01N 43/36
[52] U.S. Cl. ............................ 514/424; 514/425; 514/426; 514/428; 548/543; 548/544; 548/546; 548/557; 548/558; 548/562; 548/561
[58] Field of Search ............ 548/561, 543, 544, 546, 548/557, 558, 562; 514/428, 424, 425, 426

[56] References Cited

U.S. PATENT DOCUMENTS

| | | | |
|---|---|---|---|
| 4,567,052 | 1/1986 | Nyfeler | 548/561 |
| 5,130,328 | 7/1992 | Kameswaran | 548/561 |
| 5,157,047 | 10/1992 | Kameswaran et al. | 514/423 |
| 5,204,332 | 4/1993 | Brown et al. | 514/63 |

OTHER PUBLICATIONS

CA 109:73320h Preparation . . . herbicides. Powell et al., p. 680, 1988.
CA 113:231205p Preparation . . . agents. Brown et al., p. 706, 1990.

Primary Examiner—Mary C. Lee
Assistant Examiner—Joseph K. McKane
Attorney, Agent, or Firm—Peggy A. Climenson

[57] ABSTRACT

There are provided N-aminoalkylcarbonyloxyalkylpyrrole compounds of formula I

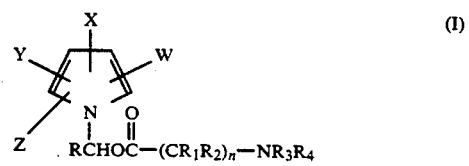

and their use for the control of insects, acarina and mollusks. Further provided are compositions and methods comprising those compounds for the protection of plants from attack by insects, acarina and mollusks.

25 Claims, No Drawings

N-AMINOALKYLCARBONYLOXYALKYLPYRROLE INSECTICIDAL ACARICIDAL AND MOLLUSCICIDAL AGENTS

BACKGROUND OF THE INVENTION

Insects, acarina and mollusks destroy growing and harvested crops. In the United States alone, agronomic crops must compete with thousands of insect and acarid species. In particular, tobacco budworms, southern armyworms and two-spotted spider mites are especially devastating to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids. Also, budworm larvae are difficult to control with currently available insecticides once they reach the third instar.

Two-spotted spider mites attack many plant species, raspberry plants for example, by removing sap from leaves. When raspberry plants are heavily infested, canes and leaves become stunted. With a severe infestation, fruiting canes are damaged, resulting in reduced yield and fruit quantity.

In spite of the commercial insecticides, acaricides and molluscicides available today, damage to crops, both growing and harvested, caused by insects, acarina and mollusks still occurs. Accordingly, there is ongoing research to create new and more effective insecticides, acaricides and molluscicides.

Certain pyrrole compounds are known to possess insecticidal, acaridical and/or molluscicidal activity (see, e.g., U.S. Pat. No. 5,157,047 and U.S. patent application Ser. Nos. 392,495 now abandoned filed on Aug. 11, 1989; 621,162 now U.S. Pat. No. 5,180,734 filed on Nov. 30, 1990; 776,967 now U.S. Pat. No. 5,162,308 filed on Oct. 15, 1991; 795,407 now U.S. Pat. No. 5,204,332 filed on Nov. 20, 1991; 803,289 filed on Dec. 4, 1991; and 971,025 filed on Nov. 3, 1992). However, none of the pyrroles disclosed in those patent applications are within the scope of the present invention.

It is therefore an object of the present invention to provide N-aminoalkylcarbonyloxyalkylpyrrole compounds which are highly effective for controlling insects, acarina and mollusks.

It is also an object of the present invention to provide a method for protecting growing plants from attack by insects, acarina and mollusks by applying to the foliage of said plants or to the soil or water in which they are growing an insecticidally, acaricidally or molluscicidally effective amount of an N-aminoalkylcarbonyloxyalkylpyrrone compound.

These and other objects of the present invention will become more apparent from the detailed description thereof set forth below.

SUMMARY OF THE INVENTION

The present invention describes N-aminoalkylcarbonyloxyalkylpyrrole compounds which are useful as insecticidal, acaricidal and molluscicidal agents for the control of insects, acarina and mollusks and for the protection of plants from attack by insects, acarina and mollusks.

The N-aminoalkylcarbonyloxyalkylpyrrole compounds of the present invention have the following structural formula I:

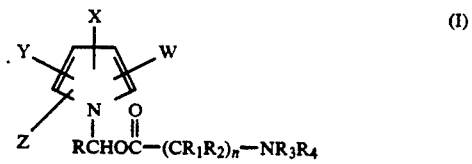

wherein
W is $CN$, $NO_2$, $S(O)_mCF_2R_5$ or

$R_5$ is hydrogen, F, Cl, Br, $CF_2H$, $CCl_2H$, $CClFH$, $CF_3$ or $CCl_3$;
m is an integer of 0, 1 or 2;
$R_6$ and $R_7$ are each independently hydrogen,
  $C_1-C_4$ alkyl optionally substituted with one or more halogen atoms, or
  phenyl optionally substituted with one or more
    halogen atoms,
    $NO_2$ groups,
    $CN$ groups,
    $C_1-C_4$ alkyl groups optionally substituted with one or more halogen atoms, or
    $C_1-C_4$ alkoxy groups optionally substituted with one or more halogen atoms;
X is halogen, $CF_3$, $CN$, $NO_2$, $S(O)_mCF_2R_5$ or
  phenyl optionally substituted with one or more
    halogen atoms,
    $NO_2$ groups,
    $CN$ groups,
    $C_1-C_4$ alkyl groups optionally substituted with one or more halogen atoms, or
    $C_1-C_4$ alkoxy groups optionally substituted with one or more halogen atoms;
Y is halogen, $CF_3$ or
  phenyl optionally substituted with one or more
    halogen atoms,
    $NO_2$ groups,
    $CN$ groups,
    $C_1-C_4$ alkyl groups optionally substituted with one or more halogen atoms, or
    $C_1-C_4$ alkoxy groups optionally substituted with one or more halogen atoms;
Z is hydrogen, halogen or $CF_3$;
R is hydrogen or $C_1-C_4$ alkyl;
$R_1$ and $R_2$ are each independently hydrogen,
  $C_1-C_6$ alkyl optionally substituted with one or more halogen atoms,
  $C_1-C_6$ alkoxy optionally substituted with one or more halogen atoms, or
  phenyl optionally substituted with one or more halogen atoms,
    $NO_2$ groups,
    $CN$ groups,
    $C_1-C_4$ alkyl groups optionally substituted with one or more halogen atoms, or
    $C_1-C_4$ alkoxy groups optionally substituted with one or more halogen atoms, or
  when $R_1$ and $R_2$ are taken together with the atom to which they are attached may form a $C_3-C_6$ cycloalkyl group optionally substituted with one to three $C_1$-$C_4$ alkyl groups, $C_2$-$C_6$ alkenyl groups or phenyl groups, or $R_1$ or $R_2$ may be taken together with $R_3$ and the atoms to which they are attached to form a 4- to 7-membered heterocyclic ring;

n is an integer of 1, 2, 3 or 4;

$R_3$ is hydrogen,
- $C_1$-$C_6$ alkyl,
- $C_2$-$C_6$ alkenyl,
- $C_2$-$C_6$ alkynyl, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms, or $R_3$ may be taken together with either $R_1$ or $R_2$ and the atoms to which they are attached to form a 4- to 7-membered heterocyclic ring;

$R_4$ is hydrogen,
- $C_1$-$C_6$ alkyl,
- $C_2$-$C_6$ alkenyl,
- $C_2$-$C_6$ alkynyl,
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms,
- $C(A)R_8$,
- $C(A)R_9$,
- CN,
- $SO_2R_{10}$, or
- $C(O)CHR_{11}NHR_{12}$;

A is O or S;

$R_8$ is $C_1$-$C_6$ alkyl optionally substituted with one to three halogen atoms,
- $C_2$-$C_6$ alkenyl,
- $C_2$-$C_6$ alkynyl, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

$R_9$ is $OR_{13}$, $CO_2R_{13}$ or $NR_{14}R_{15}$;

$R_{13}$ is $C_1$-$C_6$ alkyl optionally substituted with one phenyl group, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

$R_{14}$ and $R_{15}$ are each independently hydrogen or $C_1$-$C_4$ alkyl;

$R_{10}$ is $NR_{14}R_{15}$,
- $C_1$-$C_6$ alkyl,
- $C_2$-$C_6$ alkenyl,
- $C_2$-$C_6$ alkynyl, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

$R_{11}$ is hydrogen,
- $C_1$-$C_4$ alkyl groups optionally substituted with
  - one hydroxy group,
  - one $SR_{16}$ group,
  - one $C(O)NH_2$ group,
  - one $NH_2$ group,
  - one $NHC(=NH)NH_2$ group,
  - one $CO_2H$ group,
  - one phenyl group optionally substituted with one hydroxy group,
  - one 3-indolyl group or
  - one 4-imidazolyl group;

$R_{16}$ is hydrogen or $C_1$-$C_4$ alkyl;

$R_{12}$ is $C(A)R_{17}$; and $R_{17}$ is $C_1$-$C_6$ alkyl optionally substituted with one or more halogen atoms,
- $C_1$-$C_6$ alkoxyalkyl,
- $C_1$-$C_6$ alkylthio,
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms,
- $OR_{13}$,
- $NR_{14}R_{15}$, or
- $CO_2R_{13}$.

This invention also relates to compositions containing those compounds and methods for using those compounds and compositions. Advantageously, it has been found that the N-aminoalkylcarbonyloxyalkylpyrrole compounds of the present invention, and compositions containing them, are effective insecticidal, acaricidal and molluscicidal agents for the control of insects, acarina and mollusks and for the protection of plants from attack by insects, acarina and mollusks. The compounds of the present invention are especially useful for the control of tobacco budworms.

DETAILED DESCRIPTION OF THE INVENTION

Insects, acarina and mollusks destroy growing and harvested crops. In the United States alone, agronomic crops must compete with thousands of insect and acarid species. Accordingly, there is ongoing research to create new and more effective insecticides, acaricides and molluscicides for the control of insects, acarina and mollusks and for the protection of plants from attack by insects, acarina and mollusks. There is also ongoing research to create new insecticides and acaricides to overcome the resistance observed with several classes of insecticidal and acaricidal agents.

Advantageously, the present invention provides a method for controlling insects, acarina and mollusks by contacting said insects, acarina and mollusks, their breeding grounds, food supply or habitat with an insecticidally, acaricidally or molluscicidally effective amount of a formula I, N-aminoalkylcarbonyloxyalkylpyrrole compound.

The present invention also provides a method for protecting growing plants from attack by insects, acarina and mollusks by applying to the foliage of said plants or to the soil or water in which they are growing an insecticidally, acaricidally or molluscicidally effective amount of a formula I, N-aminoalkylcarbonyloxyalkylpyrrole compound.

The N-aminoalkylcarbonyloxyalkylpyrrole compounds of the present invention have the following structurally formula I:

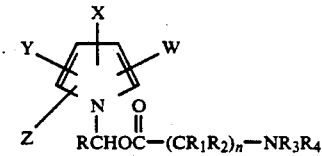
(I)

wherein
W is CN, $NO_2$, $S(O)_mCF_2R_5$ or

$R_5$ is hydrogen, F, Cl, Br, $CF_2H$, $CCl_2H$, $CClFH$, $CF_3$ or $CCl_3$;
m is an integer of 0, 1 or 2;
$R_6$ and $R_7$ are each independently hydrogen,
  $C_1$–$C_4$ alkyl optionally substituted with one or more halogen atoms, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
X is halogen, $CF_3$, CN, $NO_2$, $S(O)_mCF_2R_5$ or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
Y is halogen, $CF_3$ or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
Z is hydrogen, halogen or $CF_3$;
R is hydrogen or $C_1$–$C_4$ alkyl;
$R_1$ and $R_2$ are each independently hydrogen,
  $C_1$–$C_6$ alkyl optionally substituted with one or more halogen atoms,
  $C_1$–$C_6$ alkoxy optionally substituted with one or more halogen atoms, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms, or
  when $R_1$ and $R_2$ are taken together with the atom to which they are attached may form a $C_3$–$C_6$ cycloalkyl group optionally substituted with one to three $C_1$–$C_4$ alkyl groups, $C_2$–$C_6$ alkenyl groups or phenyl groups, or
  $R_1$ or $R_2$ may be taken together with $R_3$ and the atoms to which they are attached to form a 4- to 7-membered heterocyclic ring;
n is an integer of 1, 2, 3 or 4;
$R_3$ is hydrogen,
  $C_1$–$C_6$ alkyl,
  $C_2$–$C_6$ alkenyl,
  $C_2$–$C_6$ alkynyl, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms, or
  $R_3$ may be taken together with either $R_1$ or $R_2$ and the atoms to which they are attached to form a 4- to 7-membered heterocyclic ring;
$R_4$ is hydrogen,
  $C_1$–$C_6$ alkyl,
  $C_2$–$C_6$ alkenyl,
  $C_2$–$C_6$ alkynyl,
  phenyl optionally substituted with one or more halogen atoms,
    $NO_2$ groups,
    CN groups,
    $C_1$–$C_4$ alkyl groups optionally substituted with one or more hydrogen atoms, or
    $C_1$–$C_4$ alkoxy groups optionally substituted with one or more halogen atoms,
  $C(A)R_8$,
  $C(A)R_9$,
  CN,
  $SO_2R_{10}$, or
  $C(O)CHR_{11}NHR_{12}$;
A is O or S;
$R_8$ is $C_1$–$C_6$ alkyl optionally substituted with one to three halogen atoms,
  $C_2$–$C_6$ alkenyl,
  $C_2$–$C_6$ alkynyl, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
$R_9$ is $OR_{13}$, $CO_2R_{13}$ or $NR_{14}R_{15}$;
$R_{13}$ is $C_1$–$C_6$ alkyl optionally substituted with one phenyl group, or
  phenyl optionally substituted with one or more halogen atoms,
    $NO_2$ groups,
    CN groups, $C_1$-$C_4$ alkyl groups optionally substituted with one or more halogen atoms, or $C_1$-$C_4$ alkoxy groups optionally substituted with one or more halogen atoms;

$R_{14}$ and $R_{15}$ are each independently hydrogen or $C_1$-$C_4$ alkyl;

$R_{10}$ is $NR_{14}R_{15}$,
- $C_1$-$C_6$ alkyl,
- $C_2$-$C_6$ alkenyl,
- $C_2$-$C_6$ alkynyl, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

$R_{11}$ is hydrogen,
- $C_1$-$C_4$ alkyl groups optionally substituted with one hydroxy group,
  - one $SR_{16}$ group,
  - one $C(O)NH_2$ group,
  - one $NH_2$ group,
  - one $NHC(=NH)NH_2$ group,
  - one $CO_2H$ group,
  - one phenyl group optionally substituted with one hydroxy group,
  - one 3-indolyl group or
  - one 4-imidazolyl group;

$R_{16}$ is hydrogen or $C_1$-$C_4$ alkyl;

$R_{12}$ is $C(A)R_{17}$; and $R_{17}$ is $C_1$-$C_6$ alkyl optionally substituted with one or more halogen atoms,
- $C_1$-$C_6$ alkoxyalkyl,
- $C_1$-$C_6$ alkylthio,
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms,
- $OR_{13}$,
- $NR_{14}R_{15}$, or
- $CO_2R_{13}$.

Preferred formula I compounds of the invention are those wherein

W is CN, $NO_2$, $S(O)_mCF_2R_5$ or $$\overset{S}{\underset{\|}{C}}NR_6R_7;$$

$R_5$ is hydrogen, F, Cl, Br, $CF_2H$, $CCl_2H$, CClFH, $CF_3$ or $CCl_3$;

m is an integer of 0, 1 or 2;

$R_6$ and $R_7$ are each independently hydrogen or $C_1$-$C_4$ alkyl;

X is Cl, Br, $CF_3$ or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

Y is Cl, Br, $CF_3$ or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

Z is Cl, Br or $CF_3$;

R is hydrogen;

$R_1$ and $R_2$ are each independently hydrogen,
- $C_1$-$C_6$ alkyl optionally substituted with one or more halogen atoms, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

n is an integer of 1 or 2;

$R_3$ is hydrogen or $C_1$-$C_6$ alkyl;

$R_4$ is $C(A)R_8$, $C(A)R_9$, $SO_2R_{10}$ or $C(O)CHR_{11}NHR_{12}$;

A is O;

$R_8$ is $C_1$-$C_6$ alkyl optionally substituted with one to three halogen atoms, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

$R_9$ is $OR_{13}$ or $CO_2R_{13}$;

$R_{13}$ is $C_1$-$C_6$ alkyl optionally substituted with one phenyl group or one to three halogen atoms, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

$R_{10}$ is $C_1$-$C_6$ alkyl, or
- phenyl optionally substituted with one or more halogen atoms,
  - $NO_2$ groups,
  - CN groups,
  - $C_1$-$C_4$ alkyl groups optionally substituted with one or more halogen atoms, or
  - $C_1$-$C_4$ alkoxy groups optionally substituted with one or more halogen atoms;

$R_{11}$ is hydrogen or $C_1$-$C_4$ alkyl;

$R_{12}$ is $C(A)R_{17}$; and $R_{17}$ is $C_1$-$C_6$ alkyl optionally substituted with one or more halogen atoms, or
- phenyl optionally substituted with one or more halogen atoms,
  - $NO_2$ groups,
  - CN groups, $C_1$-$C_4$ alkyl groups optionally substituted with one or more halogen atoms, or
$C_1$-$C_4$ alkoxy groups optionally substituted with one or more halogen atoms.

More preferred insecticidal, acaricidal, and molluscicidal compounds of this invention are those wherein
W is CN or $S(O)_mCF_3$;
m is an integer of 0, 1 or 2;
X is phenyl optionally substituted with one or more halogen atoms,
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms;
Y is Cl or Br;
Z is Cl, Br or $CF_3$;
R is hydrogen;
$R_1$ and $R_2$ are each independently hydrogen,
    $C_1$-$C_6$ alkyl optionally substituted with one or more halogen atoms, or
    phenyl optionally substituted with one or more halogen atoms;
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms;
n is an integer of 1 or 2;
$R_3$ is hydrogen or $C_1$-$C_6$ alkyl;
$R_4$ is $C(A)R_9$, $SO_2R_{10}$ or $C(O)CHR_{11}NHR_{12}$;
A is O;
$R_8$ is $C_1$-$C_6$ alkyl optionally substituted with one to three halogen atoms, or
    phenyl optionally substituted with one or more halogen atoms,
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms;
$R_9$ is $OR_{13}$ or $CO_2R_{13}$;
$R_{13}$ is $C_1$-$C_6$ alkyl optionally substituted with one phenyl group or one to three halogen atoms;
$R_{10}$ is phenyl optionally substituted with one or more halogen atoms,
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms;
$R_{11}$ is hydrogen;
$R_{12}$ is $C(A)R_{17}$; and
$R_{17}$ is phenyl optionally substituted with one or more halogen atoms,
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms.

Most preferred compounds of this invention which are especially effective insecticidal, acaricidal and molluscicidal agents are those having the structural formula II:

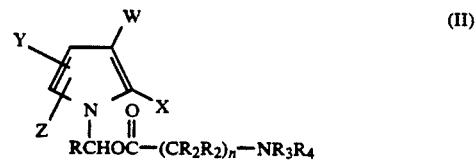

wherein
W is CN or $S(O)_mCF_3$;
m is an integer of 0, 1 or 2;
X is phenyl optionally substituted with one or more halogen atoms,
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms;
Y is Cl or Br;
Z is Cl, Br or $CF_3$;
R is hydrogen;
$R_1$ and $R_2$ are each independently hydrogen,
    $C_1$-$C_6$ alkyl optionally substituted with one or more halogen atoms, or
    phenyl optionally substituted with one or more halogen atoms;
    $NO_3$ groups,
    CN groups,
    $C_1$-$C_4$ alkyl groups optionally substituted with one or more halogen atoms, or
    $C_1$-$C_4$ alkoxy groups optionally substituted with one or more halogen atoms;
n is an integer of 1 or 2;
$R_3$ is hydrogen or $C_1$-$C_6$ alkyl;
$R_4$ is $C(A)R_8$, $C(A)R_9$, $SO_2R_{10}$ or $C(O)CHR_{11}NHR_{12}$;
A is O;
$R_8$ is $C_1$-$C_6$ alkyl optionally substituted with one to three halogen atoms, or
    phenyl optionally substituted with one or more halogen atoms,
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms;
$R_9$ is $OR_{13}$ or $CO_2R_{13}$;
$R_{13}$ is $C_1$-$C_6$ alkyl optionally substituted with one phenyl group or one to three halogen atoms;
$R_{10}$ is phenyl optionally substituted with one or more halogen atoms,
    $NO_2$ groups,
    CN groups,
    $C_1$-$C_4$ alkyl groups optionally substituted with one or more halogen atoms, or
    $C_1$-$C_4$ alkoxy groups optionally substituted with one or more halogen atoms;
$R_{11}$ is hydrogen;
$R_{12}$ is $C(A)R_{17}$; and
$R_{17}$ is phenyl optionally substituted with one or more halogen atoms,
    $NO_2$ groups, CN groups, $C_1$–$C_4$ alkyl groups optionally substituted with one or more halogen atoms, or $C_1$–$C_4$ alkoxy groups optionally substituted with one or more halogen atoms.

Exemplary of halogen hereinabove are fluorine, chlorine, bromine and iodine.

Advantageously, it has been found that the formula I compounds of the present invention are especially useful for the control of tobacco budworms, southern armyworms and two-spotted spider mites.

Formula I compounds may be prepared as shown in Flow Diagram I.

FLOW DIAGRAM I

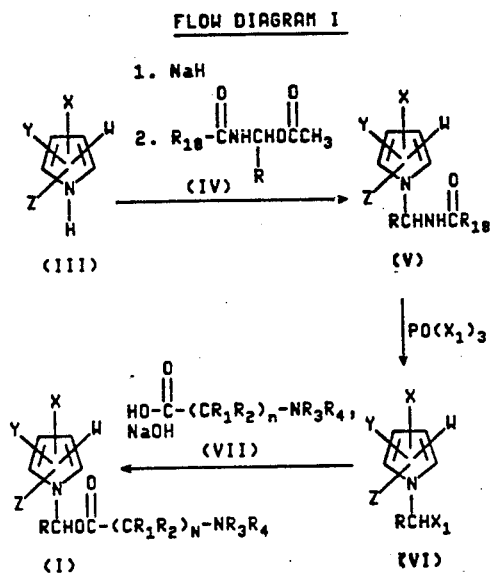

wherein
$R_{18}$ is $C_1$–$C_6$ alkyl optionally substituted with one to three halogen atoms,
phenyl optionally substituted with one or two halogen, CN, $NO_2$, $C_1$–$C_4$ alkyl, $C_1$–$C_4$ alkoxy or $CF_3$ groups,
2- or 3-thienyl or
2- or 3-furyl;
$X_1$ is Cl or Br; and
W, X, Y, Z, R, $R_1$, $R_2$, $R_3$, $R_4$ and n are as described hereinabove for formula I.

The appropriately substituted pyrrole of formula III is reacted with an alkylating agent of formula IV in the presence of an alkali metal hydride or an alkali metal $C_1$–$C_6$ alkoxide to form an N-alkanoylaminomethyl or N-aroylaminomethylpyrrole of formula V, said formula V aminomethylpyrrole is then reacted with an excess of phosphorus oxychloride or phosphorus oxybromide to form a 1-halomethylpyrrole of formula VI. Said 1-halomethylpyrrole is reacted with a carboxylic acid or formula VII in the presence of an alkali metal hydroxide, such as sodium or potassium hydroxide, to form desired N-aminoalkylcarbonyloxyalkylpyrrole of formula I.

Starting formula III pyrrole compounds may be prepared according to the procedure described in U.S. Pat. No. 5,157,047 and U.S. patent application Ser. Nos. 392,495 now abandoned filed on Aug. 11, 1989; 621,162 now U.S. Pat. No. 5,180,734 filed on Nov. 30, 1990; 776,967 now U.S. Pat. No. 5,102,308 filed on Oct. 15, 1991; 795,407 now U.S. Pat. No. 5,204,332 filed on Nov. 20, 1991; 803,289 filed on Dec. 4, 1991; and 971,025 filed on Nov. 3, 1992 and are incorporated herein by reference thereto. Starting formula IV alkylating agents are described in U.S. patent application Ser. No. 755,935 filed on Sep. 6, 1991 and is incorporated herein by reference thereto. In addition, certain formula VI 1-halomethylpyrrole compounds wherein W is CN may be prepared as described in U.S. Pat. No. 5,118,816.

The N-aminoalkylcarbonyloxyalkylpyrrole compounds of the present invention are effective for controlling insects, acarina and mollusks. Those compounds are also effective for protecting growing or harvested crops from attack by insects and acarina.

Insects controlled by the formula I compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms and mustard beetles; and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites. Mollusks controlled by the compounds of this invention include gastropoda such as snails, slugs, cowries and limpets. Advantageously, it has been found that the compounds of the present invention are especially effective against tobacco budworm third-instar larvae, southern armyworms and two-spotted spider mites.

In practice, generally about 10 ppm to 10,000 ppm and preferably about 100 ppm to 5,000 ppm of a formula I N-aminoalkylcarbonyloxyalkylpyrrole compound, dispered in water or another liquid carrier, is effective when applied to the plants, the crops or the soil in which said crops are growing to protect said crops from attack by insects, acarina and mollusks.

The formula I compounds of this invention are also effective for controlling insects, acarina and mollusks, when applied to the foliage of plants and/or to the soil or water in which said plants are growing in sufficient amount to provide a rate of from about 0.100 kg/ha to 4.0 kg/ha of active ingredient.

While the compounds of this invention are effective for controlling insects, acarina and mollusks when employed alone, they may also be used in combination with other biological chemicals, including other insecticides, acaricides and molluscicides. For example, the formula I compounds of this invention may be used effectively in conjunction or combination with pyrethroids, phosphates, carbamates, cyclodienes, endotoxin of bacillus thuringiensis (Bt), formamidines, phenol tin compounds, chlorinated hydrocarbons, benzoylphenyl ureas and the like.

The compounds of this invention may be formulated as emulsifiable concentrates, flowable concentrates, or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with inert, solid or liquid diluents.

For example, wettable powders, dusts, and dust concentrate formulations can be prepared by grinding and blending together about 25% to about 85% by weight of Formula I compounds and about 75% to about 15% by weight of a solid diluent such as bentonite, diatomaceous earth, kaolin, attapulgite, or the like, about 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol or the like.

A typical emulsifiable concentrate can be prepared by dissolving about 15% to about 70% by weight of an N-aminoalkylcarbonyloxyalkylpyrrole compound in about 85% to about 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

An especially effective method for controlling terrestrial gastropods with the formula I compounds of the invention, is to proffer the active molluscicidal material in the form of a bait formulation. These bait formulations can be widely varied but generally contain about 1% to 20% by weight of the active ingredient, about 40% to 50% by weight of solid edible nutritive substance, about 5% to 10% by weight of a carbohydrate source such as sugar, molasses, corn syrup or the like and the remainder of the formulation, i.e. about 30% to 50% by weight of water or other consumable liquid.

In order to facilitate a further understanding of the invention, the following examples are presented to illustrative more specific details thereof. The invention is not to be limited thereby except as defined in the claims.

EXAMPLE 1

Preparation of [3-Chloro-5-(p-chlorophenyl)-4-cyano-5-(trifluoromethyl)pyrrol-1-yl]methyl N-(N-benzoylglycyl)glycinate

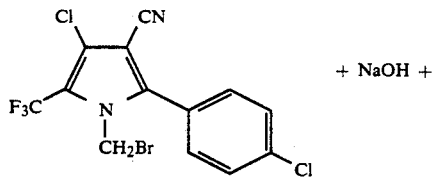

+ NaOH +

1-(Bromomethyl)-4-chloro-2-(p-chlorophenyl)-5-(trifluoromethyl)pyrrole-3-carbonitrile (2.0 g, 5.02 mmol) is added to a mixture of benzoylglycylglycine (1.41 g, 5.97 mmol) and sodium hydroxide (0.25 g, 6.0 mmol) in N,N-dimethylformamide. The reaction mixture is stirred overnight at room temperature, diluted with water and extracted with ethyl acetate. The combined organic extracts are washed sequentially with water and brine, dried over $MgSO_4$ and concentrated in vacuo to obtain a brown oil. The oil is chromatographed using silica gel and a 60:40 methylene chloride/ethyl acetate mixture to give the title product as a tan solid (1.55 g, mp 65°-67° C.).

Using essentially the same procedure, but substituting the appropriately substituted 1-(halomethyl)-2-arylpyrrole for 1-(bromomethyl)-4-chloro-2-(p-chlorophenyl)-5-(trifluoromethyl)pyrrole-3-carbonitrile and the appropriately substituted carboxylic acid for benzoylglycylglycine, the following compounds are obtained:

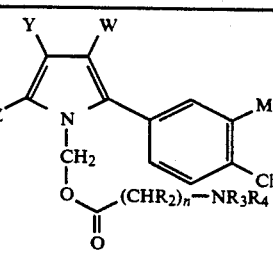

| M | W | Y | Z | $R_2$ | n | $R_3$ | $R_4$ | mp°C. |
|---|---|---|---|---|---|---|---|---|
| H | CN | Cl | $CF_3$ | H | 1 | H | $-C(O)OCH_2C_6H_5$ | glass |
| H | CN | Cl | $CF_3$ | H | 1 | H | $-C(O)-(p-Cl-C_6H_5)$ | 162-163 |
| H | CN | Br | $CF_3$ | H | 2 | H | $-C(O)-(p-F-C_6H_5)$ | 139-141 |
| H | CN | Br | $CF_3$ | $-(p-Cl-C_6H_5)$ | 1 | H | $-C(O)OC(CH_3)_3$ | 115-117 |
| H | CN | Br | $CF_3$ | H | 1 | H | $-C(O)-(p-Cl-C_6H_5)$ | 73-75 |
| H | CN | Cl | $CF_3$ | H | 1 | H | $-C(O)C_6H_5$ | 149-150 |
| H | CN | Cl | $CF_3$ | H | 1 | H | $-C(O)CH_3$ | 86-88 |
| H | CN | Cl | $CF_3$ | H | 2 | H | $-C(O)CF_3$ | 110-111 |
| H | CN | Cl | $CF_3$ | H | 1 | $CH_3$ | $-C(O)C(O)OC_2H_5$ | 141-143 |

-continued

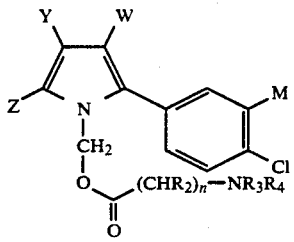

| M | W | Y | Z | R₂ | n | R₃ | R₄ | mp°C. |
|---|---|---|---|---|---|---|---|---|
| H | CN | Cl | CF₃ | H | 1 | H | —S(O)₂C₆H₅ | 100-102 |
| H | CN | Cl | CF₃ | —CH(CH₃)₂ | 1 | H | —S(O)₂—(p-Cl—C₆H₅) | 148-149 |
| H | S(O)₂CF₃ | Br | Br | H | 1 | H | —C(O)—(p-Cl—C₆H₅) | 74-78 |
| Cl | CN | Cl | Cl | H | 1 | H | —C(O)—(p-Cl—C₆H₅) | 111-116 |
| H | CN | Cl | CF₃ | H | 1 | H | —C(O)CH₃ | oil |

EXAMPLE 2

Insecticide and Acaricide Evaluations

The following tests show the efficacy of the compounds as insecticides and acaricides. The evaluations are conducted with solutions of test compounds dissolved or dispersed in 50/50 acetone/water mixtures. The test compound is technical material dissolved or dispersed in said acetone/water mixtures in sufficient amount to provide the concentrations set forth in Table I below.

All concentrations reported herein are in terms of active ingredient. All tests are conducted in a laboratory maintained at about 27° C. The rating system employed is as follows:

| Rating System |
|---|
| 0 = no effect |
| 1 = 10-25% kill |
| 2 = 26-35% kill |
| 3 = 36-45% kill |
| 4 = 46-55% kill |
| 5 = 56-65% kill |
| 6 = 66-75% kill |
| 7 = 76-85% kill |
| 8 = 86-99% kill |
| 9 = 100% kill |
| — = no evaluation |

The test species of insects used in the present evaluations along with specific test procedures are described below.

*Spodoptera eridania* 3rd instar larvae, southern armyworm

A sieva lima bean leaf expanded to 7 to 8 cm in length is dipped in the test suspension with agitation for 3 seconds and placed in a hood to dry. The leaf is then placed in a 100×10 mm petri dish containing a damp filter paper on the bottom and 10 3rd instar caterpillars. The dish is maintained for 5 days before observations are made of mortality, reduced feeding or any interference with normal moulting.

*Tetranychus urticae* (OP-resistant strain), 2-spotted spider mite

Sieva lima bean plants with primary leaves expanded to 7 to 8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test formulation for 3 seconds with agitation and set in the hood to dry. Plants are kept for 2 days before estimates of adult kill are made.

*Empoasca abrupta*, adults, western potato leafhopper

A sieva lima bean leaf about 5 cm long is dipped in the test formulation for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

*Heliothis virenscens*, 3rd instar tobacco budworm

Cotton cotyledons are dipped in the test formulation and allowed to dry in a hood. When dry, each is cut into quarters and ten sections placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Diabrotic undecimpunctata howardi*, 3rd instar southern corn rootworm

One cc of fine talc is placed in a 30 mL wide-mouth screw-top glass jar. One mL of the appropriate acetone test solution is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jars are capped and the contents thoroughly mixed on a Vortex Mixer. Following this, ten 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 to 10 kg/ha, respectively.

The data obtained for the above described evaluations are reported in Table I.

TABLE I

| | Insecticide and Acaricide Evaluations | | | | | | | | | | | |
|---|---|---|---|---|---|---|---|---|---|---|---|---|
| | Armyworm (ppm) | | | OP-Resistant Mites (ppm) | | Leaf hopper (ppm) | | Tobacco Budworm (ppm) | | | Southern Corn Rootworm (kg/ha) | |
| Compound | 1000 | 100 | 10 | 300 | 100 | 100 | 10 | 1000 | 100 | 10 | 50 | 10 |
| [3-Chloro-5-(p-chlorophenyl)-4-cyano-2-(trifluoromethyl)pyrrol-1-yl]methyl N-(p-chlorobenzoyl)glycinate | 9 | 9 | 9 | 9 | 7 | 9 | 9 | 9 | 9 | 9 | 9 | 5 |
| [3-Bromo-5-(p-chlorophenyl)-4-cyano-2-(trifluoromethyl)pyrrol-1-yl]methyl N-(p-fluorobenzoyl)-beta-alaninate | 9 | 9 | 9 | 6 | — | 0 | — | 9 | 9 | 7 | 6.5 | 3 |
| [3-Bromo-5-(p-chlorophenyl)-4-cyano-2-(trifluoromethyl)pyrrol-1-yl]methyl N-tertbutyl N-carboxy-2-(p-chlorophenyl)glycinate ester | 9 | 9 | 6 | 9 | 9 | 0 | 0 | 9 | 9 | 0 | 9 | 4 |
| [3-Bromo-5-(p-chlorophenyl)-4-cyano-2-(trifluoromethyl)pyrrol-1-yl]methyl N-(p-chlorobenzoyl)glycinate | 9 | 9 | 9 | 2 | — | 6.5 | 0 | 9 | 9 | 9 | 0 | — |
| [3-Chloro-5-(p-chlorophenyl)-4-cyano-2-(trifluoromethyl)pyrrol-1-yl]methyl N-benzoylglycinate | 9 | 9 | 9 | 5 | — | 9 | 9 | 9 | 9 | 9 | 8.5 | 3 |
| [3-Chloro-5-(p-chlorophenyl)-4-cyano-2-(trifluoromethyl)pyrrol-1-yl]methyl N-acetylglycinate | 9 | 9 | 9 | 9 | 9 | 5 | 0 | 9 | 9 | 8 | 9 | 8 |
| [3-Chloro-5-(p-chlorophenyl)-4-cyano-2-(trifluoromethyl)pyrrol-1-yl]methyl N-(trifluoroacetyl)-beta-alaninate | 9 | 9 | 9 | 0 | 9 | 0 | 0 | 9 | 9 | 0 | 9 | 6 |
| [3-Chloro-5-(p-chlorophenyl)-4-cyano-2-(trifluoromethyl)pyrrol-1-yl]methyl ethyl (carboxymethyl)methyloxamate ester | 9 | 9 | 9 | 0 | 5 | 9 | 8.5 | 9 | 9 | 9 | 8.5 | 6 |
| [2,3-Dichloro-4-cyano-5-(3,4-dichlorophenyl)-pyrrol-1-yl]methyl N-(p-chlorobenzoyl)glycinate | 9 | 9 | 9 | 0 | — | 2.5 | 0 | 9 | 9 | 0 | 3.5 | 0 |
| [3-Chloro-5-(p-chlorophenyl)-4-cyano-2-(trifluoromethyl)pyrrol-1-yl]methyl N-(phenylsulfonyl)glycinate | 9 | 9 | 9 | 7 | 9 | 6 | — | 9 | 9 | 4 | 0 | — |
| [3-Chloro-5-(p-chlorophenyl)-4-cyano-2-(trifluoromethyl)pyrrol-1-yl]methyl N-[(p-chlorophenyl)sulfonyl]-2-isopropylglycinate | 9 | 9 | 0 | 0 | — | 0 | — | 9 | 9 | 0 | 0 | — |
| [3-Chloro-5-(p-chlorophenyl)-4-cyano-2-(trifluoromethyl)pyrrol-1-yl]methyl N-(trifluoroacetyl)glycinate | 9 | 9 | 9 | 9 | 8 | 9 | 9 | — | 9 | 0 | 9 | 2 |
| {2,3-Dibromo-5-(p-chlorophenyl)-4-[(trifluoromethyl)sulfonyl]pyrrol-1-yl}methyl N-(p-chlorobenzoyl)glycinate | 9 | 9 | 1 | 9 | 0 | 0 | 0 | 9 | 9 | 0 | 3.5 | 0 |
| [3-Chloro-5-(p-chlorophenyl)-4-cyano-5-(trifluoromethyl)pyrrol-1-yl]methyl N-(N-benzoylglycyl)glycinate | 9 | — | — | 0 | — | — | — | — | — | — | 8 | — |
| [3-Chloro-5-(p-chlorophenyl)-4-cyano-2-(tri- | 9 | — | — | 0 | — | — | — | — | — | — | 9 | — |

TABLE I-continued

| | Insecticide and Acaricide Evaluations | | | | | | | | | | | |
|---|---|---|---|---|---|---|---|---|---|---|---|---|
| | Armyworm (ppm) | | | OP-Resistant Mites (ppm) | | Leaf hopper (ppm) | | Tobacco Budworm (ppm) | | | Southern Corn Rootworm (kg/ha) | |
| Compound | 1000 | 100 | 10 | 300 | 100 | 100 | 10 | 1000 | 100 | 10 | 50 | 10 |
| fluoromethyl)pyrrol-1-yl]methyl N-benzyl N-carboxyglycinate ester | | | | | | | | | | | | |

We claim:
1. A compound having the structural formula

$$\begin{array}{c} X \\ Y \diagup\!\!\!\diagdown W \\ | \quad | \\ Z \quad N \quad O \\ | \quad \| \\ RCHOC-(CR_1R_2)_n-NR_3R_4 \end{array}$$

wherein
W is CN, NO$_2$, S(O)$_m$CF$_2$R$_5$ or $$\begin{array}{c} S \\ \| \\ CNR_6R_7; \end{array}$$

R$_5$ is hydrogen, F, Cl, Br, CF$_2$H, CCl$_2$H, CClFH, CF$_3$ or CCl$_3$;
m is an integer of 0, 1 or 2;
R$_6$ and R$_7$ are each independently hydrogen,
 C$_1$-C$_4$ alkyl optionally substituted with one or more halogen atoms, or
 phenyl optionally substituted with one or more halogen atoms,
  NO$_2$ groups,
  CN groups,
  C$_1$-C$_4$ alkyl groups optionally substituted with one or more halogen atoms, or
  C$_1$-C$_4$ alkoxy groups optionally substituted with one or more halogen atoms;
X is halogen, CF$_3$, CN, NO$_2$, S(O)$_m$CF$_2$R$_5$ or
 phenyl optionally substituted with one or more halogen atoms,
  NO$_2$ groups,
  CN groups,
  C$_1$-C$_4$ alkyl groups optionally substituted with one or more halogen atoms, or
  C$_1$-C$_4$ alkoxy groups optionally substituted with one or more halogen atoms;
Y is halogen, CF$_3$ or
 phenyl optionally substituted with one or more halogen atoms,
  NO$_2$ groups,
  CN groups,
  C$_1$-C$_4$ alkyl groups optionally substituted with one or more halogen atoms, or
  C$_1$-C$_4$ alkoxy groups optionally substituted with one or more halogen atoms;
Z is hydrogen, halogen or CF$_3$;
R is hydrogen or C$_1$-C$_4$ alkyl;
R$_1$ and R$_2$ are each independently hydrogen,
 C$_1$-C$_6$ alkyl optionally substituted with one or more halogen atoms,
 C$_1$-C$_6$ alkoxy optionally substituted with one or more halogen atoms, or
 phenyl optionally substituted with one or more halogen atoms,
  NO$_2$ groups,
  CN groups,
  C$_1$-C$_4$ alkyl groups optionally substituted with one or more halogen atoms, or
  C$_1$-C$_4$ alkoxy groups optionally substituted with one or more halogen atoms, or
 when R$_1$ and R$_2$ are taken together with the atom to which they are attached may form a C$_3$-C$_6$ cycloalkyl group optionally substituted with one to three C$_1$-C$_4$ alkyl groups, C$_2$-C$_6$ alkenyl groups or phenyl groups, or
 R$_1$ or R$_2$ may be taken together with R$_3$ and the atoms to which they are attached to form a 4- to 7-membered heterocyclic ring;
n is an integer of 1, 2, 3 or 4;
R$_3$ is hydrogen,
 C$_1$-C$_6$ alkyl,
 C$_2$-C$_6$ alkenyl,
 C$_2$-C$_6$ alkynyl, or
 phenyl optionally substituted with one or more halogen atoms,
  NO$_2$ groups,
  CN groups,
  C$_1$-C$_4$ alkyl groups optionally substituted with one or more halogen atoms, or
  C$_1$-C$_4$ alkoxy groups optionally substituted with one or more halogen atoms, or
 R$_3$ may be taken together with either R$_1$ or R$_2$ and the atoms to which they are attached to form a 4- to 7-membered heterocyclic ring;
R$_4$ is hydrogen,
 C$_1$-C$_6$ alkyl,
 C$_2$-C$_6$ alkenyl,
 C$_2$-C$_6$ alkynyl,
 phenyl optionally substituted with one or more halogen atoms,
  NO$_2$ groups,
  CN groups,
  C$_1$-C$_4$ alkyl groups optionally substituted with one or more halogen atoms, or
  C$_1$-C$_4$ alkoxy groups optionally substituted with one or more halogen atoms,
 C(A)R$_8$,
 C(A)R$_9$,
 CN,
 SO$_2$R$_{10}$, or
 C(O)CHR$_{11}$NHR$_{12}$;
A is O or S;
R$_8$ is C$_1$-C$_6$ alkyl optionally substituted with one to three halogen atoms,
 C$_2$-C$_6$ alkenyl,
 C$_2$-C$_6$ alkynyl, or
 phenyl optionally substituted with one or more halogen atoms, NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

R$_9$ is OR$_{13}$, CO$_2$R$_{13}$ or NR$_{14}$R$_{15}$;

R$_{13}$ is C$_1$–C$_6$ alkyl optionally substituted with one phenyl group, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

R$_{14}$ and R$_{15}$ are each independently hydrogen or C$_1$–C$_4$ alkyl;

R$_{10}$ is NR$_{14}$R$_{15}$,
C$_1$–C$_6$ alkyl,
C$_2$–C$_6$ alkenyl,
C$_2$–C$_6$ alkynyl, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

R$_{11}$ is hydrogen,
C$_1$–C$_4$ alkyl groups optionally substituted with
one hydroxy group,
one SR$_{16}$ group,
one C(O)NH$_2$ group,
one NH$_2$ group,
one NHC(=NH)NH$_2$ group,
one CO$_2$H group,
one phenyl group optionally substituted with one hydroxy group,
one 3-indolyl group or
one 4-imidazolyl group;

R$_{16}$ is hydrogen or C$_1$–C$_4$ alkyl;

R$_{12}$ is C(A)R$_{17}$; and

R$_{17}$ is C$_1$–C$_6$ alkyl optionally substituted with one or more halogen atoms,
C$_1$–C$_6$ alkoxyalkyl,
C$_1$–C$_6$ alkylthio,
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms,
OR$_{13}$,
NR$_{14}$R$_{15}$, or
CO$_2$R$_{13}$.

2. The compound according to claim 1 wherein
W is CN, NO$_2$, S(O)$_m$CF$_2$R$_5$ or

R$_5$ is hydrogen, F, Cl, Br, CF$_2$H, CCl$_2$H, CClFH, CF$_3$ or CCl$_3$;

m is an integer of 0, 1 or 2;

R$_6$ and R$_7$ are each independently hydrogen or C$_1$–C$_4$ alkyl;

X is Cl, Br, CF$_3$ or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

Y is Cl, Br, CF$_3$ or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

Z is Cl, Br or CF$_3$;

R is hydrogen;

R$_1$ and R$_2$ are each independently hydrogen,
C$_1$–C$_6$ alkyl optionally substituted with one or more halogen atoms, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

n is an integer of 1 or 2;

R$_3$ is hydrogen or C$_1$–C$_6$ alkyl;

R$_4$ is C(A)R$_8$, C(A)R$_9$, SO$_2$R$_{10}$ or C(O)CHR$_{11}$NHR$_{12}$;

A is O;

R$_8$ is C$_1$–C$_6$ alkyl optionally substituted with one to three halogen atoms, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

R$_9$ is OR$_{13}$ or CO$_2$R$_{13}$;

R$_{13}$ is C$_1$–C$_6$ alkyl optionally substituted with one phenyl group or one to three halogen atoms, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;

R$_{10}$ is C$_1$–C$_6$ alkyl, or
phenyl optionally substituted with one or more halogen atoms,
NO$_2$ groups,
CN groups, $C_1$–$C_4$ alkyl groups optionally substituted with one or more halogen atoms, or $C_1$–$C_4$ alkoxy groups optionally substituted with one or more halogen atoms;

$R_{11}$ is hydrogen or $C_1$–$C_4$ alkyl;

$R_{12}$ is $C(A)R_{17}$; and $R_{17}$ is $C_1$–$C_6$ alkyl optionally substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms.

3. The compound according to claim 2 wherein

W is CN or $S(O)_mCF_3$;

m is an integer of 0, 1 or 2;

X is phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Y is Cl or Br;

Z is Cl, Br or $CF_3$;

R is hydrogen;

$R_1$ and $R_2$ are each independently hydrogen, $C_1$–$C_6$ alkyl optionally substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

n is an integer of 1 or 2;

$R_3$ is hydrogen or $C_1$–$C_6$ alkyl;

$R_4$ is $C(A)R_8$, $C(A)R_9$, $SO_2R_{10}$ or $C(O)CHR_{11}NHR_{12}$;

A is O;

$R_8$ is $C_1$–$C_6$ alkyl optionally substituted with one to three halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

$R_9$ is $OR_{13}$ or $CO_2R_{13}$;

$R_{13}$ is $C_1$–$C_6$ alkyl optionally substituted with one phenyl group or one to three halogen atoms;

$R_{10}$ is phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

$R_{11}$ is hydrogen;

$R_{12}$ is $C(A)R_{17}$; and $R_{17}$ is phenyl optionally substituted with one or more halogen atoms, CN groups, $C_1$–$C_4$ alkyl groups optionally substituted with one or more halogen atoms, or $C_1$–$C_4$ alkoxy groups optionally substituted with one or more halogen atoms.

4. The compound according to claim 3 wherein the compound has the structural formula

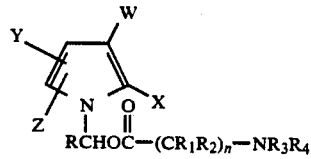

5. The compound according to claim 4 [3-chloro-5-(p-chlorophenyl)-4-cyano-2-(trifluoromethyl)pyrrol-1-yl]methyl N-(p-chlorobenzoyl)glycinate.

6. The compound according to claim 4 [3-chloro-5-(p-chlorophenyl-4-cyano-2-(trifluoromethyl)pyrrol-1-yl]methyl ethyl (carboxymethyl)methyloxamate ester.

7. The compound according to claim 4 [3-chloro-5-(p-chlorophenyl)-4-cyano-2-(trifluoromethyl)pyrrol-1-yl]methyl N-acetylglycinate.

8. The compound according to claim 4 [3-bromo-5-(p-chlorophenyl)-4-cyano-2-(trifluoromethyl)pyrrol-1-yl]methyl N-(p-fluorobenzoyl)beta-alaninate.

9. The compound according to claim 4 [3-chloro-5-(p-chlorophenyl)-4-cyano-2-(trifluoromethyl)pyrrol-1-yl]methyl N-benzoylglycinate.

10. The compound according to claim 4 [3-bromo-5-(p-chlorophenyl)-4-cyano-2-(trifluoromethyl)pyrrol-1-yl]methyl N-(p-chlorobenzoyl)glycinate.

11. The compound according to claim 4 [3-chloro-5-(p-chlorophenyl)-4-cyano-2-(trifluoromethyl)pyrrol-1-yl]methyl N-(phenylsulfonyl)glycinate.

12. A method for controlling insects, acarina and mollusks which comprises contacting said insects, acarina and mollusks, their breeding grounds, food supply or habitat with an insecticidally, acaricidally and molluscicidally effective amount of a compound having the structural formula

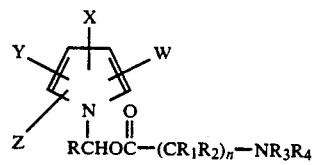

wherein

W is CN, $NO_2$, $S(O)_mCF_2R_5$ or $$\underset{CNR_6R_7}{\overset{S}{\|}};$$

$R_5$ is hydrogen, F, Cl, Br, $CF_2H$, $CCl_2H$, $CClFH$, $CF_3$ or $CCl_3$;

m is an integer of 0, 1 or 2;

$R_6$ and $R_7$ are each independently hydrogen, $C_1$–$C_4$ alkyl optionally substituted with one or more halogen atoms, or phenyl optionally substituted with one or more halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms;

X is halogen, CF$_3$, CN, NO$_2$, S(O)$_m$CF$_2$R$_5$ or
phenyl optionally substituted with one or more
halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms;

Y is halogen, CF$_3$ or
phenyl optionally substituted with one or more
halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms;

Z is hydrogen, halogen or CF$_3$;

R is hydrogen or C$_1$-C$_4$ alkyl;

R$_1$ and R$_2$ are each independently hydrogen,
C$_1$-C$_6$ alkyl optionally substituted with one or more halogen atoms,
C$_1$-C$_6$ alkoxy optionally substituted with one or more halogen atoms, or
phenyl optionally substituted with one or more halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms, or when R$_1$ and R$_2$ are taken together with the atom to which they are attached may form a C$_3$-C$_6$ cycloalkyl group optionally substituted with one to three C$_1$-C$_4$ alkyl groups, C$_2$-C$_6$ alkenyl groups or phenyl groups, or R$_1$ or R$_2$ may be taken together with R$_3$ and the atoms to which they are attached to form a 4- to 7-membered heterocyclic ring;

n is an integer of 1, 2, 3 or 4;

R$_3$ is hydrogen,
C$_1$-C$_6$ alkyl,
C$_2$-C$_6$ alkenyl,
C$_2$-C$_6$ alkynyl, or
phenyl optionally substituted with one or more
halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms, or
R$_3$ may be taken together with either R$_1$ or R$_2$ and the atoms to which they are attached to form a 4- to 7-membered heterocyclic ring;

R$_4$ is hydrogen,
C$_1$-C$_6$ alkyl,
C$_2$-C$_6$ alkenyl,
C$_2$-C$_6$ alkynyl,
phenyl optionally substituted with one or more
halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms,
C(A)R$_8$,
C(A)R$_9$,
CN,
SO$_2$R$_{10}$, or
C(O)CHR$_{11}$NHR$_{12}$;

A is O or S;

R$_8$ is C$_1$-C$_6$ alkyl optionally substituted with one to three halogen atoms,
C$_2$-C$_6$ alkenyl,
C$_2$-C$_6$ alkynyl, or
phenyl optionally substituted with one or more
halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms;

R$_9$ is OR$_{13}$, CO$_2$R$_{13}$ or NR$_{14}$R$_{15}$;

R$_{13}$ is C$_1$-C$_6$ alkyl optionally substituted with one phenyl group, or
phenyl optionally substituted with one or more
halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms;

R$_{14}$ and R$_{15}$ are each independently hydrogen or C$_1$-C$_4$ alkyl;

R$_{10}$ is NR$_{14}$R$_{15}$,
C$_1$-C$_6$ alkyl,
C$_2$-C$_6$ alkenyl,
C$_2$-C$_6$ alkynyl, or
phenyl optionally substituted with one or more
halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms;

R$_{11}$ is hydrogen,
C$_1$-C$_4$ alkyl groups optionally substituted with
one hydroxy group,
one SR$_{16}$ group,
one C(O)NH$_2$ group,
one NH$_2$ group,
one NHC(=NH)NH$_2$ group,
one CO$_2$H group,
one phenyl group optionally substituted with one hydroxy group,
one 3-indolyl group or
one 4-imidazolyl group;

R$_{16}$ is hydrogen or C$_1$-C$_4$ alkyl;

R$_{12}$ is C(A)R$_{17}$; and

R$_{17}$ is C$_1$-C$_6$ alkyl optionally substituted with one or more halogen atoms,
C$_1$-C$_6$ alkoxyalkyl, $C_1-C_6$ alkylthio,
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms,
$OR_{13}$,
$NR_{14}R_{15}$, or
$CO_2R_{13}$.

13. The method according to claim 12 wherein
W is CN, $NO_2$, $S(O)_mCF_2R_5$ or

$R_5$ is hydrogen, F, Cl, Br, $CF_2H$, $CCl_2H$, $CClFH$, $CF_3$ or $CCl_3$;
m is an integer of 0, 1 or 2;
$R_6$ and $R_7$ are each independently hydrogen or $C_1-C_4$ alkyl;
X is Cl, Br, $CF_3$ or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;
Y is Cl, Br, $CF_3$ or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;
Z is Cl, Br or $CF_3$;
R is hydrogen;
$R_1$ and $R_2$ are each independently hydrogen,
$C_1-C_6$ alkyl optionally substituted with one or more halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;
n is an integer of 1 or 2;
$R_3$ is hydrogen or $C_1-C_6$ alkyl;
$R_4$ is $C(A)R_8$, $C(A)R_9$, $SO_2R_{10}$ or $C(O)CHR_{11}NHR_{12}$;
A is O;
$R_8$ is $C_1-C_6$ alkyl optionally substituted with one to three halogen atoms, or
phenyl optionally substituted with one or more halogen atoms,
$NO_3$ groups,
CN groups,
$C_1-C_4$ alkyl groups optionally substituted with one or more halogen atoms, or
$C_1-C_4$ alkoxy groups optionally substituted with one or more halogen atoms;
$R_9$ is $OR_{13}$, $CO_2R_{13}$ or $NR_{14}R_{15}$;
$R_{13}$ is $C_1-C_6$ alkyl optionally substituted with one phenyl group or one to three halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;
$R_{10}$ is $C_1-C_6$ alkyl, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;
$R_{11}$ is hydrogen or $C_1-C_4$ alkyl;
$R_{12}$ is $C(A)R_{17}$; and
$R_{17}$ is $C_1-C_6$ alkyl optionally substituted with one or more halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms.

14. The method according to claim 13 wherein
W is CN or $S(O)_mCF_3$;
m is an integer of 0, 1 or 2;
X is phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;
Y is Cl or Br;
Z is Cl, Br or $CF_3$;
R is hydrogen;
$R_1$ and $R_2$ are each independently hydrogen,
$C_1-C_6$ alkyl optionally substituted with one or more halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;
n is an integer of 1 or 2;
$R_3$ is hydrogen or $C_1-C_6$ alkyl;
$R_4$ is $C(A)R_8$, $C(A)R_9$, $SO_2R_{10}$ or $C(O)CHR_{11}NHR_{12}$;
A is O;
$R_8$ is $C_1-C_6$ alkyl optionally substituted with one to three halogen atoms, or
phenyl optionally substituted with one or more halogen atoms, NO₂ groups,
CN groups,
C₁-C₄ alkyl groups optionally substituted with one or more halogen atoms, or
C₁-C₄ alkoxy groups optionally substituted with one or more halogen atoms;

$R_9$ is $OR_{13}$ or $CO_2R_{13}$;

$R_{13}$ is C₁-C₆ alkyl optionally substituted with one phenyl group or one to three halogen atoms;

$R_{10}$ is phenyl optionally substituted with one or more halogen atoms,
NO₂ groups,
CN groups,
C₁-C₄ alkyl groups optionally substituted with one or more halogen atoms, or
C₁-C₄ alkoxy groups optionally substituted with one or more halogen atoms;

$R_{11}$ is hydrogen;

$R_{12}$ is $C(A)R_{17}$; and $R_{17}$ is phenyl optionally substituted with one or more halogen atoms,
NO₂ groups,
CN groups,
C₁-C₄ alkyl groups optionally substituted with one or more halogen atoms, or
C₁-C₄ alkoxy groups optionally substituted with one or more halogen atoms.

15. The method according to claim 14 wherein the compound has the structural formula

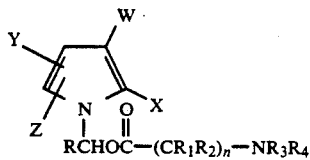

16. The method according to claim 15 wherein the compound is selected from the group consisting of
[3-chloro-5-(p-chlorophenyl)-4-cyano-2-(trifluoromethyl)pyrrol-1-yl]methyl N-(p-chlorobenzoyl)glycinate;
[3-chloro-5-(p-chlorophenyl-4-cyano-2-(trifluoromethyl)pyrrol-1-yl]methyl ethyl (carboxymethyl)methyloxamate ester;
[3-chloro-5-(p-chlorophenyl)-4-cyano-2-(trifluoromethyl)pyrrol-1-yl]methyl N-acetylglycinate;
[3-bromo-5-(p-chlorophenyl)-4-cyano-2-(trifluoromethyl)pyrrol-1-yl]methyl N-(p-fluorobenzoyl)betaalaninate;
[3-chloro-5-(p-chlorophenyl)-4-cyano-2-(trifluoromethyl)pyrrol-1-yl]methyl N-benzoylglycinate;
[3-bromo-5-(p-chlorophenyl)-4-cyano-2-(trifluoromethyl)pyrrol-1-yl]methyl N-(p-chlorobenzoyl)glycinate; and
[3-chloro-5-(p-chlorophenyl)-4-cyano-2-(trifluoromethyl)pyrrol-1-yl]methyl N-(phenylsulfonyl)glycinate.

17. A method for protecting growing plants from attack by insects, acarina and mollusks which comprises applying to the foliage of said plants or to the soil or water in which they are growing an insecticidally, acaricidally or molluscicidally effective amount of a compound having the structural formula

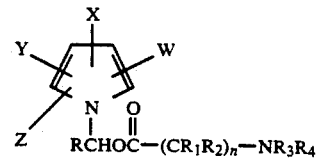

wherein W, X, Y, Z, R, $R_1$, $R_2$, $R_3$, $R_4$ and n are as described in claim 12.

18. The method according to claim 17 wherein
W is CN, NO₂, $S(O)_mCF_2R_5$ or

$R_5$ is hydrogen, F, Cl, Br, $CF_2H$, $CCl_2H$, $CClFH$, $CF_3$ or $CCl_3$;

m is an integer of 0, 1 or 2;

$R_6$ and $R_7$ are each independently hydrogen or C₁-C₄ alkyl;

X is Cl, Br, $CF_3$ or
phenyl optionally substituted with one or more halogen atoms,
NO₂ groups,
CN groups,
C₁-C₄ alkyl groups optionally substituted with one or more halogen atoms, or
C₁-C₄ alkoxy groups optionally substituted with one or more halogen atoms;

Y is Cl, Br, $CF_3$ or
phenyl optionally substituted with one or more halogen atoms,
NO₂ groups,
CN groups,
C₁-C₄ alkyl groups optionally substituted with one or more halogen atoms, or
C₁-C₄ alkoxy groups optionally substituted with one or more halogen atoms;

Z is Cl, Br or $CF_3$;

R is hydrogen;

$R_1$ and $R_2$ are each independently hydrogen,
C₁-C₆ alkyl optionally substituted with one or more halogen atoms, or
phenyl optionally substituted with one or more halogen atoms,
NO₂ groups,
CN groups,
C₁-C₄ alkyl groups optionally substituted with one or more halogen atoms, or
C₁-C₄ alkoxy groups optionally substituted with one or more halogen atoms;

n is an integer of 1 or 2;

$R_3$ is hydrogen or C₁-C₆ alkyl;

$R_4$ is $C(A)R_8$, $C(A)R_9$, $SO_2R_{10}$ or $C(O)CHR_{11}NHR_{12}$;

A is O;

$R_8$ is C₁-C₆ alkyl optionally substituted with one to three halogen atoms, or
phenyl optionally substituted with one or more halogen atoms,
NO₂ groups,
CN groups,
C₁-C₄ alkyl groups optionally substituted with one or more halogen atoms, or $C_1-C_4$ alkoxy groups optionally substituted with one or more halogen atoms;

$R_9$ is $OR_{13}$ or $CO_2R_{13}$;

$R_{13}$ is $C_1-C_6$ alkyl optionally substituted with one phenyl group or one to three halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;

$R_{10}$ is $C_1-C_6$ alkyl, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;

$R_{11}$ is hydrogen or $C_1-C_4$ alkyl;

$R_{12}$ is $C(A)R_{17}$; and $R_{17}$ is $C_1-C_6$ alkyl optionally substituted with one or more halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms.

19. The method according to claim 18 wherein

W is CN or $S(O)_mCF_3$;

m is an integer of 0, 1 or 2;

X is phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;

Y is Cl or Br;

Z is Cl, Br or $CF_3$;

R is hydrogen;

$R_1$ and $R_2$ are each independently hydrogen,
$C_1-C_6$ alkyl optionally substituted with one or more halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;

n is an integer of 1 or 2;

$R_3$ is hydrogen or $C_1-C_6$ alkyl;

$R_4$ is $C(A)R_8$, $C(A)R_9$, $SO_2R_{10}$ or $C(O)NHR_{11}NHR_{12}$;

A is O;

$R_8$ is $C_1-C_6$ alkyl optionally substituted with one to three halogen atoms, or
phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;

$R_9$ is $OR_{13}$ or $CO_2R_{13}$;

$R_{13}$ is $C_1-C_6$ alkyl optionally substituted with one phenyl group or one to three halogen atoms;

$R_{10}$ is phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms;

$R_{11}$ is hydrogen;

$R_{12}$ is $C(A)R_{17}$; and $R_{17}$ is phenyl optionally substituted with one or more halogen atoms,
$NO_2$ groups,
CN groups,
$C_1-C_4$ alkyl groups optionally substituted with one or more halogen atoms, or
$C_1-C_4$ alkoxy groups optionally substituted with one or more halogen atoms.

20. The method according to claim 19 wherein the compound has the structural formula

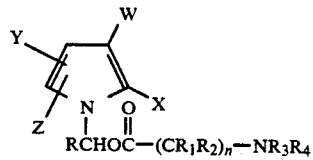

21. The method according to claim 20 wherein the compound is selected from the group consisting of

[3-chloro-5-(p-chlorophenyl)-4-cyano-2-(trifluoromethyl)pyrrol-1-yl]methyl N-(p-chlorobenzoyl)glycinate;

[3-chloro-5-(p-chlorophenyl-4-cyano-2-(trifluoromethyl)pyrrol-1-yl]methyl ethyl (carboxymethyl)methyloxamate ester;

[3-chloro-5-(p-chlorophenyl)-4-cyano-2-(trifluoromethyl)pyrrol-1-yl]methyl N-acetylglycinate;

[3-bromo-5-(p-chlorophenyl)-4-cyano-2-(trifluoromethyl)pyrrol-1-yl]methyl N-(p-fluorobenzoyl)-betaalaninate;

[3-chloro-5-(p-chlorophenyl)-4-cyano-2-(trifluoromethyl)pyrrol-1-yl]methyl N-benzoylglycinate;

[3-bromo-5-(p-chlorophenyl)-4-cyano-2-(trifluoromethyl)pyrrol-1-yl]methyl N-(p-chlorobenzoyl)glycinate; and

[3-chloro-5-(p-chlorophenyl)-4-cyano-2-(trifluoromethyl)pyrrol-1-yl]methyl N-(phenylsulfonyl)glycinate.

22. The method according to claim 17 wherein the compound is applied to the plants or soil in which they are growing at a rate of about 0.100 kg/ha to 4.0 kg/ha.

23. A composition for controlling insects, acarina and mollusks comprising an agronomically acceptable carrier and an insecticidally, molluscicidally or acaricidally effective amount of a compound having the structural formula

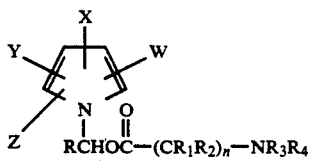

wherein W, X, Y, Z, R, R$_1$, R$_2$, R$_3$, R$_4$ and n are as described in claim 12.

24. The composition according to claim 23 wherein W is CN, NO$_2$, S(O)$_m$CF$_2$R$_5$ or

R$_5$ is hydrogen, F, Cl, Br, CF$_2$H, CCl$_2$H, CClFH, CF$_3$ or CCl$_3$;
m is an integer of 0, 1 or 2;
R$_6$ and R$_7$ are each independently hydrogen or C$_1$-C$_4$ alkyl;
X is Cl, Br, CF$_3$ or
  phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
Y is Cl, Br, CF$_3$ or
  phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
Z is Cl, Br or CF$_3$;
R is hydrogen;
R$_1$ and R$_2$ are each independently hydrogen,
  C$_1$-C$_6$ alkyl optionally substituted with one or more halogen atoms, or
  phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
n is an integer of 1 or 2;
R$_3$ is hydrogen or C$_1$-C$_6$ alkyl;
R$_4$ is C(A)R$_8$, C(A)R$_9$, SO$_2$R$_{10}$ or C(O)CHR$_{11}$NHR$_{12}$;
A is O;
R$_8$ is C$_1$-C$_6$ alkyl optionally substituted with one to three halogen atoms, or
  phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
R$_9$ is OR$_{13}$ or CO$_2$R$_{13}$;
R$_{13}$ is C$_1$-C$_6$ alkyl optionally substituted with one phenyl group or one to three halogen atoms, or
  phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
R$_{10}$ is C$_1$-C$_6$ alkyl, or
  phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
R$_{11}$ is hydrogen or C$_1$-C$_4$ alkyl;
R$_{12}$ is C(A)R$_{17}$; and
R$_{17}$ is C$_1$-C$_6$ alkyl optionally substituted with one or more halogen atoms, or
  phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms.

25. The composition according to claim 24 wherein
W is CN or S(O)$_m$CF$_3$;
m is an integer of 0, 1 or 2;
X is phenyl optionally substituted with one or more
    halogen atoms,
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
Y is Cl or Br;
Z is Cl, Br or CF$_3$;
R is hydrogen;
R$_1$ and R$_2$ are each independently hydrogen,
  C$_1$-C$_6$ alkyl optionally substituted with one or more halogen atoms, or
  phenyl optionally substituted with one or more halogen atoms;
    NO$_2$ groups,
    CN groups,
    C$_1$-C$_4$ alkyl groups optionally substituted with one or more halogen atoms, or
    C$_1$-C$_4$ alkoxy groups optionally substituted with one or more halogen atoms;
n is an integer of 1 or 2;
R$_3$ is hydrogen or C$_1$-C$_6$ alkyl;
R$_4$ is C(A)R$_9$, SO$_2$R$_{10}$ or C(O)CHR$_{11}$NHR$_{12}$;
A is O;
R$_8$ is C$_1$-C$_6$ alkyl optionally substituted with one to three halogen atoms, or
  phenyl optionally substituted with one or more halogen atoms,
    NO$_2$ groups, CN groups,
C$_1$-C$_4$ alkyl groups optionally substituted with one or more halogen atoms, or
C$_1$-C$_4$ alkoxy groups optionally substituted with one or more halogen atoms;

R$_9$ is OR$_{13}$ or CO$_2$R$_{13}$;

R$_{13}$ is C$_1$-C$_6$ alkyl optionally substituted with one phenyl group or one to three halogen atoms;

R$_{10}$ is phenyl optionally substituted with one or more halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms;

R$_{11}$ is hydrogen;

R$_{12}$ is C(A)R$_{17}$; and

R$_{17}$ is phenyl optionally substituted with one or more halogen atoms,
NO$_2$ groups,
CN groups,
C$_1$-C$_4$ alkyl groups optionally substituted with one or more halogen atoms, or
C$_1$-C$_4$ alkoxy groups optionally substituted with one or more halogen atoms.

* * * * *

UNITED STATES PATENT AND TRADEMARK OFFICE
CERTIFICATE OF CORRECTION

PATENT NO. : 5,286,743
DATED : February 15, 1994
INVENTOR(S) : David G. Kuhn et al.

It is certified that error appears in the above-indentified patent and that said Letters Patent is hereby corrected as shown below:

<u>Claim 13, column 27, line 65</u>　　should read

--"$NO_2$ groups,"--

<u>Claim 13, column 28, line 3</u>　　should read

--"$R_9$ is $OR_{13}$ or $CO_2R_{13}$;"--

<u>Claim 25, column 34, line 62</u>　　should read

--"$R_4$ is $C(A)R_8$, $C(A)R_9$, $SO_2R_{10}$ or $C(O)CHR_{11}NHR_{12}$;"--

Signed and Sealed this

Thirty-first Day of December, 1996

Attest:

BRUCE LEHMAN

*Attesting Officer*　　*Commissioner of Patents and Trademarks*